United States Patent
Fasciano et al.

(10) Patent No.: US 6,540,658 B1
(45) Date of Patent: Apr. 1, 2003

(54) LEFT-RIGHT FLOW CONTROL ALGORITHM IN A TWO CHAMBER CARDIAC PROSTHESIS

(75) Inventors: Robert W. Fasciano, Reading, MA (US); Farhad Zarinetchi, Chelmsford, MA (US)

(73) Assignee: Abiomed, Inc., Danvers, MA (US)

( * ) Notice: Subject to any disclaimer, the term of this patent is extended or adjusted under 35 U.S.C. 154(b) by 146 days.

(21) Appl. No.: 09/689,935

(22) Filed: Oct. 12, 2000

Related U.S. Application Data

(60) Provisional application No. 60/207,816, filed on May 30, 2000.

(51) Int. Cl.$^7$ ................................................ A61M 1/10
(52) U.S. Cl. ........................ 600/17; 623/3.21; 623/3.28
(58) Field of Search ...................... 600/17, 16; 623/3.1, 623/3.16, 3.21, 3.28, 3.26

(56) References Cited

U.S. PATENT DOCUMENTS

| | | |
|---|---|---|
| 3,206,768 A | 9/1965 | Preston |
| 3,426,743 A | 2/1969 | Chestnut et al. |
| 3,430,624 A | 3/1969 | Flanagan et al. |
| 3,599,244 A | 8/1971 | Wortman |
| 3,636,570 A | 1/1972 | Nielson ............................. 3/1 |
| 3,663,966 A | 5/1972 | Lavigne ............................ 3/1 |
| 3,668,708 A | 6/1972 | Tindal ............................... 3/1 |
| 3,734,648 A | 5/1973 | Nielson ...................... 417/310 |
| 3,771,174 A | 11/1973 | Wortman |
| 3,783,453 A | 1/1974 | Bolie |
| 3,824,420 A | 7/1974 | Stegeman et al. ............. 310/89 |
| 3,842,440 A | 10/1974 | Karlson ............................. 3/1 |
| 3,878,567 A | 4/1975 | Purdy ............................. 3/1.7 |
| 3,919,722 A | 11/1975 | Harmison ....................... 3/1.7 |
| 3,966,358 A | 6/1976 | Heimes et al. |
| 4,105,016 A * | 8/1978 | Donovan, Jr. ............... 415/900 |
| 4,133,616 A | 1/1979 | Poirier ....................... 417/384 |
| 4,162,543 A | 7/1979 | Shumakov et al. ............. 3/1.7 |
| 4,231,354 A | 11/1980 | Kurtz et al. |
| 4,255,821 A | 3/1981 | Carol et al. ..................... 3/1.7 |

(List continued on next page.)

OTHER PUBLICATIONS

Kung, et al., "Progress in the Development of the Abiomed Total Artificial Heart," Progress in the Abiomed TAH, Slide Forum—Artificial Hearts, Heart Valves, and Surgery 1, *ASAIO Journal*, 1995, vol. 41, pp M245–M248.

(List continued on next page.)

*Primary Examiner*—Kennedy Schaetzle
(74) *Attorney, Agent, or Firm*—Nutter, McClennen & Fish, LLP; Thomas Engellenner

(57) ABSTRACT

A biventricular cardiac prosthesis has a flow balance control system to balance blood flow through the left and right sides of the prosthesis to maintain a patient's left atrial pressure within physiologic bounds. The prosthesis can be configured to have flow characteristics so that a signal representative of the difference in hydraulic pumping pressures on the left and right sides of the prosthesis is representative of the difference between left and right atrial pressures of a patient having the prosthesis implanted. This signal can be used as a control signal to drive the prosthesis so that left atrial pressure is approximately equal to right atrial pressure, and within physiologic bounds. A specific prosthesis includes left and right pumping sections, each having a blood pumping chamber and a hydraulic fluid chamber, with a reciprocating hydraulic pump driving systole alternately on the right and left sides. A hydraulic balance chamber is hydraulically coupled to the right hydraulic fluid chamber and an adjustable occluder varies flow resistance through the hydraulic coupling. The occluder can be adjusted based on the control signal to adjustably derate right side blood flow to achieve the desired pressure balance, or the occluder can be adjusted based on fluid communication with sources of pressure in the prosthesis that are representative of right and left atrial pressures.

20 Claims, 10 Drawing Sheets

U.S. PATENT DOCUMENTS

| | | | |
|---|---|---|---|
| 4,296,500 A | 10/1981 | Monties et al. ................. | 3/1.7 |
| 4,369,530 A | 1/1983 | Robinson et al. | |
| 4,588,404 A | 5/1986 | Lapeyre | |
| 4,600,405 A | 7/1986 | Zibelin .......................... | 623/3 |
| 4,650,485 A | 3/1987 | Della Sala ..................... | 623/3 |
| 4,652,265 A | 3/1987 | McDougall .................... | 623/3 |
| 4,662,358 A | 5/1987 | Farrar et al. ................. | 128/1 D |
| 4,666,443 A | 5/1987 | Portner .......................... | 623/3 |
| 4,781,716 A | 11/1988 | Richelsoph .................... | 623/3 |
| 4,820,300 A | 4/1989 | Pierce et al. ................... | 623/3 |
| 4,822,357 A | 4/1989 | Forster et al. ................ | 623/3 |
| 4,888,011 A | 12/1989 | Kung et al. .................... | 623/3 |
| 4,981,484 A | 1/1991 | Holfert et al. ................. | 623/3 |
| 5,030,197 A | 7/1991 | Kageyama | |
| 5,041,748 A | 8/1991 | Huber .......................... | 310/80 |
| 5,100,374 A | 3/1992 | Kageyama | |
| 5,227,062 A | 7/1993 | Olsen ...................... | 210/321.6 |
| 5,267,940 A | 12/1993 | Moulder | |
| 5,300,111 A | 4/1994 | Panton et al. .................. | 623/3 |
| 5,314,469 A | 5/1994 | Gao .............................. | 623/3 |
| 5,352,180 A | 10/1994 | Candelon et al. | |
| 5,385,581 A | 1/1995 | Bramm et al. | |
| 5,743,845 A | 4/1998 | Runge .......................... | 600/16 |
| 5,809,831 A | 9/1998 | Nagai et al. ............... | 74/89.15 |
| 5,809,833 A | 9/1998 | Newport et al. ........... | 74/89.15 |
| 5,819,345 A | 10/1998 | Basgall .......................... | 5/616 |
| 5,888,242 A | 3/1999 | Antaki et al. .................. | 623/3 |
| 5,895,421 A | 4/1999 | Nakhmanson ................ | 623/3 |
| 5,980,571 A | 11/1999 | Nomura et al. | |
| 6,176,822 B1 | 1/2001 | Nix et al. | |

OTHER PUBLICATIONS

Parnis et al., "Chronic In Vivo Evaluation of an Electrohydraulic Total Artificial Heart," Slide Forum—CVS 6, *ASAIO Journal*, 1994, pp M489–M493.

Kung et al., "Self–Regulation of an Electrohydraulic Total Artificial Heart," *Artificial Heart 3*, Akutsu et al., ed. Springer–Verlag, 1991, pp 173–180.

Kung et al., "An Atrial Hydraulic Shunt in a Total Artificial Heart, A Balance Mechanism for the Bronchial Shunt," *ASAIO Journal*, vol. 39, No. 3, Jul.–Sep. 1993, pp M213–M217.

Yu et al., "A Compact and Noise Free Electrohydraulic Total Artificial Heart," *ASAIO Journal*, vol. 39, No. 3, Jul.–Sep. 1993, pp M386–M391.

Olsen et al., *Simplified right–left balance for the implanted artificial heart*, Artificial Heart 3, Proceedings of the $3^{rd}$. International Symposium on Artificial Heart and Assist Devices, pp. 235–245, 1990.

Rosenberg et al., *An Electric Motor–Driven Total Artificial Heart: Seven Months Survival in the Calf*, vol. XXX Trans. Am Soc. Artif. Intern Organs, pp. 69–74, 1984.

Takatani, et al., *Optimum Control Mode for a Total Artificial Heart*, vol. XXVIII Trans. Am. Soc. Artif. Intern Organs, pp. 148–153, 1982.

Kung et al., *A Unique Left–Right Flow Balance Compensation Scheme for an Implantable Total Artificial Heart*, ASAIO Transactions, pp. 468–470, 1989.

Lioi et al., *In Vitro Development of Automatic Control for the Actively Filled Electrohydraulic Heart*, Artificial Organs—Raven Press Ltd., pp. 152–162, 1987.

Tanaka, et al., *Factors Affecting Left–Right Heart Output Differences in Artificial Heart Implanted Animals*, vol. XXX1 Trans. Am. Soc. Artif. Intern. Organs, pp. 211–215, 1985.

Lioi, Ph. D. et al., *Physiological Control of Electric Total Artificial Hearts*, Devices and Technology Contractors Meeting, Program and Abstracts, Dec. 16–18, 1985, p. 89.

\* cited by examiner

LEFT-RIGHT FLOW CONTROL ALGORITHM IN A TWO CHAMBER CARDIAC PROSTHESIS

RELATED APPLICATIONS

This application claims priority from United States provisional patent application Ser. No. 60/207,816, filed May 30, 2000. This application is related to United States application Ser. No. 09/687,603 and 09/687,040, filed on even date herewith.

BACKGROUND OF THE INVENTION

This invention relates in general to artificial hearts and more particularly to an artificial heart system that will respond to varying physiological demand and includes mechanisms accommodating the actual flow imbalance between pulmonary and systemic circulations.

Despite steady progress in developing a permanent artificial heart for long term implantation in a patient as a substitute for a failed natural heart, a number of issues must still be resolved. Among the issues that need to be addressed in an untethered artificial heart system are control strategies that respond to varying physiological demand, and mechanisms for accommodating the flow imbalance between the pulmonary and systemic circulations.

Left-right cardiac output differences have been well documented. Physiologically, the volume of blood flow pumped by the left side of the heart is higher than that pumped by the right side of the heart. This difference is largely attributable to a circulatory pathway known as the bronchial shunt. This flow originates in the left arterial system, passes through the bronchial tissue and then returns directly to the left atrium. This difference typically appears to be up to about ten percent of cardiac output with the left side flow always greater than the right side flow. Artificial heart systems must account for this inherent physiological circulatory imbalance. In addition, sources of flow imbalance can be man-made. For example, differences in regurgitation through artificial valves provided on the left and right sides can introduce a flow imbalance. Artificial heart systems must account for these types of circulating imbalances as well.

Pressure in the right atrium (RAP or right atrial pressure) is generally determined by the venous return into the heart and cardiac output. Average RAP typically ranges from 3 to 15 mmHg, depending on the physiology of the individual and that individual's current activity level. Average LAP (left atrial pressure) typically ranges from 3 to 18 mmHg. In a biventricular cardiac prosthesis, controlling LAP within a physiologic range is important. If LAP is consistently high, not only can the atrium itself be damaged, but the high pressure can, in extreme cases, result in pulmonary edema or excessive fluid retention of the lungs. Also, when LAP is too low, atrial damage, air emboli and in-flow limitations can result. It is thus an important goal of any flow balance control in a biventricular cardiac prosthesis system to maintain LAP within a physiologic range. It can also be beneficial to balance pressure between the left and right sides of an artificial heart to maintain LAP within a physiologic range, both to maintain LAP and RAP in balance, and also to regulate LAP without directly measuring LAP. Direct measurement of LAP can be problematic, however, because it generally involves placement of a pressure transducer directly in contact with blood flowing through the left atrium, with the attendant potential problems such as thromboembolism.

In one known flow balance approach, controlled outflow valve regurgitation in the right chambers of one artificial heart is employed. (Lioi, A. P.; Kolff, W. D.; Olsen, D. B.; Crump, K.; Isaacson, M. S.; and Nielson, S. D.; "Physiological Control of Electric Total Artificial Hearts", in Devices and Contractors Branch Contractors Meeting 1985, Program and Abstracts, Dec. 1985, 89.) In this approach the left and right sides of the heart are pumped alternately by a reversing hydraulic pump and a deliberate outflow leakage is designed into the right pump to accommodate the flow difference. However the regurgitant flow is only a function of the square root of the difference between the pulmonary diastolic pressure and the right atrial pressure. This results in a near constant compensating flow which may well be inadequate to accommodate differences. Also, changes in the orifice size over the long duration can cause this flow imbalance to drift from the preset value.

A second prior art approach employs a gas compliance chamber and passive filling to accommodate the flow difference in conjunction with a stroke-time division scheme. (Rosenberg, G.; Snyder, J.; Landis, D. L.; Geselowitz, D. B.; Donachy, J. H.; and Pierce, W. S., "An Electric Motor-Driven Total Artificial Heart: Seven Months Survival In The Calf", Trans Am Soc Artif Intern Organ, 15, 69, 1984.) The use of a gas compliance chamber leads to maintenance problems in maintaining the composition and pressure of the gas over time.

A further method and system for derating right side flow is described in Kung et al, U.S. Pat. No. 4,888,011 (incorporated herein by reference in its entirety). Kung provides a biventricular cardiac prosthesis having left and right side hydraulic chambers and left and right side blood pumping chambers which replace the natural ventricles in a patient with a failing heart. Also included is a reciprocating hydraulic pump that pumps hydraulic fluid back and forth between the right and left hydraulic chambers to drive right and left systole. Kung further provides a hydraulic compliance chamber having a flexible membrane coupled to the left atrial blood. During periods of higher left atrial pressure, hydraulic fluid is at least partially shunted to the hydraulic flow of the right pump, thus reducing the stroke volume and output of the right side. The Kung device relies on pressure in the hydraulic pumping chambers for pressure representative of respective atrial pressures. While this approximation of atrial pressure is sufficient to improve flow balance under a variety of conditions, the approximation can be less accurate under high blood flow conditions.

SUMMARY OF THE INVENTION

The invention provides a biventricular cardiac prosthesis having a flow control system for maintaining left atrial pressure within physiologic bounds. That is, the prosthesis flow control is responsive to left atrial pressure to maintain that pressure within physiologic bounds. In one aspect of the invention, a method for controlling a biventricular cardiac prosthesis measures a patient's left atrial pressure, determines whether the left atrial pressure is outside of a desired tolerance about a desired left atrial pressure value, and derates right side blood flow to maintain left atrial pressure within the tolerance. An apparatus of this aspect of the invention includes left and right pumping sections, a right pumping section pumping volume derating element, and a control element controlling the derating of right side flow to maintain a patient's left atrial pressure within physiologic bounds. The measurement of left atrial pressure may be taken directly, or indirectly as described hereinbelow.

In another aspect, the invention provides a method and apparatus for balancing flow by derating right side flow to hold a patient's left atrial pressure close to the patient's right atrial pressure, that is, the difference between left atrial pressure and right atrial pressure is close to zero. An apparatus of this aspect is a cardiac prosthesis that includes left and right hydraulic pumping chambers and a reciprocating hydraulic pump for alternately driving left and right systole. A control signal can be derived from the difference in pressure between the left and right hydraulic pumping chambers, and the control signal is applied to adjust the flow of the right hydraulic pumping chamber to maintain the control signal close to zero.

In another aspect, the invention provides a system and method for measuring the difference between right and left atrial pressures in a patient having a biventricular prosthesis. This system includes a prosthesis selected so as to have similar flow or pressure drop characteristics for blood inflow on its left and right sides and has one or more pressure transducers for measuring average diastolic pressures in its left and right pumping chambers. The difference between left and right atrial pressure in a patient having the prosthesis installed can then be determined from the difference in pressure between the left and right pumping chambers. In one embodiment, an energy converter having a hydraulic pump and a fluid switch drives left and right systole in the prosthesis. A single pressure transducer is provided in the hydraulic pump inlet to measure both left and right diastolic pressures. In this embodiment of the invention, the use of a single transducer to measure both pressures and then taking the difference between the two signals results in the desired measurement signal while eliminating any inaccuracies due to "drift" that may occur in the transducer over time.

In a second embodiment of this aspect of the invention, the hydraulic pump is stopped for a short period of time to allow the hydraulic pressure in the left and right pumping chambers to equilibrate. Separate transducers measuring left and right hydraulic pressures are then polled and a difference is taken as an offset. This offset is then applied to difference measurements taken during operation of the prosthesis as a representation of transducer drift over time. In still another embodiment of this aspect of the invention, the speed of the to hydraulic pump is varied according to a profile rather than stopped at the end of systole. Because this difference between left and right side pressure at this time is proportional to the square of the pump speed (which is known), with two or more measurements at different speeds, the pressure difference at a pump speed or zero (the transducer offset) can be extrapolated.

In still another aspect of the invention, a total artificial heart with controlled left and right flow is provided. The total artificial heart has left and right pumping sections, each having a blood pumping chamber connectable to a patient's atrium for blood inflow, and a hydraulic pumping section. A reciprocating pump causes hydraulic fluid to flow back and forth between the right and left hydraulic pumping sections. A hydraulic balance chamber responsive to the patient's left atrial pressure is in hydraulic communication with the right hydraulic pumping section by means of a hydraulic coupling with flow through the coupling between the right hydraulic pumping section and the hydraulic balance chamber affecting the stroke volume of the right hydraulic pumping section. The hydraulic coupling has a variable flow resistance that is adjustable to maintain a desired control of flow between the right and left pumping sections. In one embodiment, the resistance to flow in the coupling is adjusted by adjusting an occluder that effectively restricts a cross-sectional dimension of the coupling to increase resistance to flow, or alternatively increases a cross-sectional dimension to reduce resistance to flow.

In a further specific embodiment using active flow control, the total artificial heart is designed as described above so that the difference between left and right pumping section pressure is representative of the difference between left and right atrial pressure in a patient having the total artificial heart implanted. A signal representing the difference between left and right hydraulic pumping section pressures can then be used to automatically adjust the occluder to modify the right hydraulic section stroke volume to maintain the patient's left atrial pressure close to the patient's right atrial pressure, and thus within physiologic bounds.

In a further aspect of the invention, passive control is employed to maintain a patient's left atrial pressure within physiologic bounds. In one embodiment of this aspect, a total artificial heart has left and right pumping sections, with a hydraulic balance chamber hydraulically coupled to a hydraulic pumping section of the right side. The hydraulic coupling includes a variable flow resistance that is adjustable to maintain balanced flow between the right and left pumping sections. The variable flow resistance can be provided by a variable orifice having a movable flow restrictor. The movable flow restrictor has a first side coupled to a pressure source representative of left atrial pressure and a second opposed side coupled to a pressure source representative of right atrial pressure so that the movable flow restrictor moves in response to differences between the two atrial pressures.

In a further embodiment, the hydraulic balance chamber is coupled to a patient's left atrium to serve as a source representative of left atrial pressure, and the right hydraulic section serves as a source representative of right atrial pressure.

BRIEF DESCRIPTION OF THE DRAWINGS

The invention will be more fully understood from the following detailed description taken in conjunction with the accompanying drawings, in which.

DETAILED DESCRIPTION OF THE DRAWINGS

Figure 1:
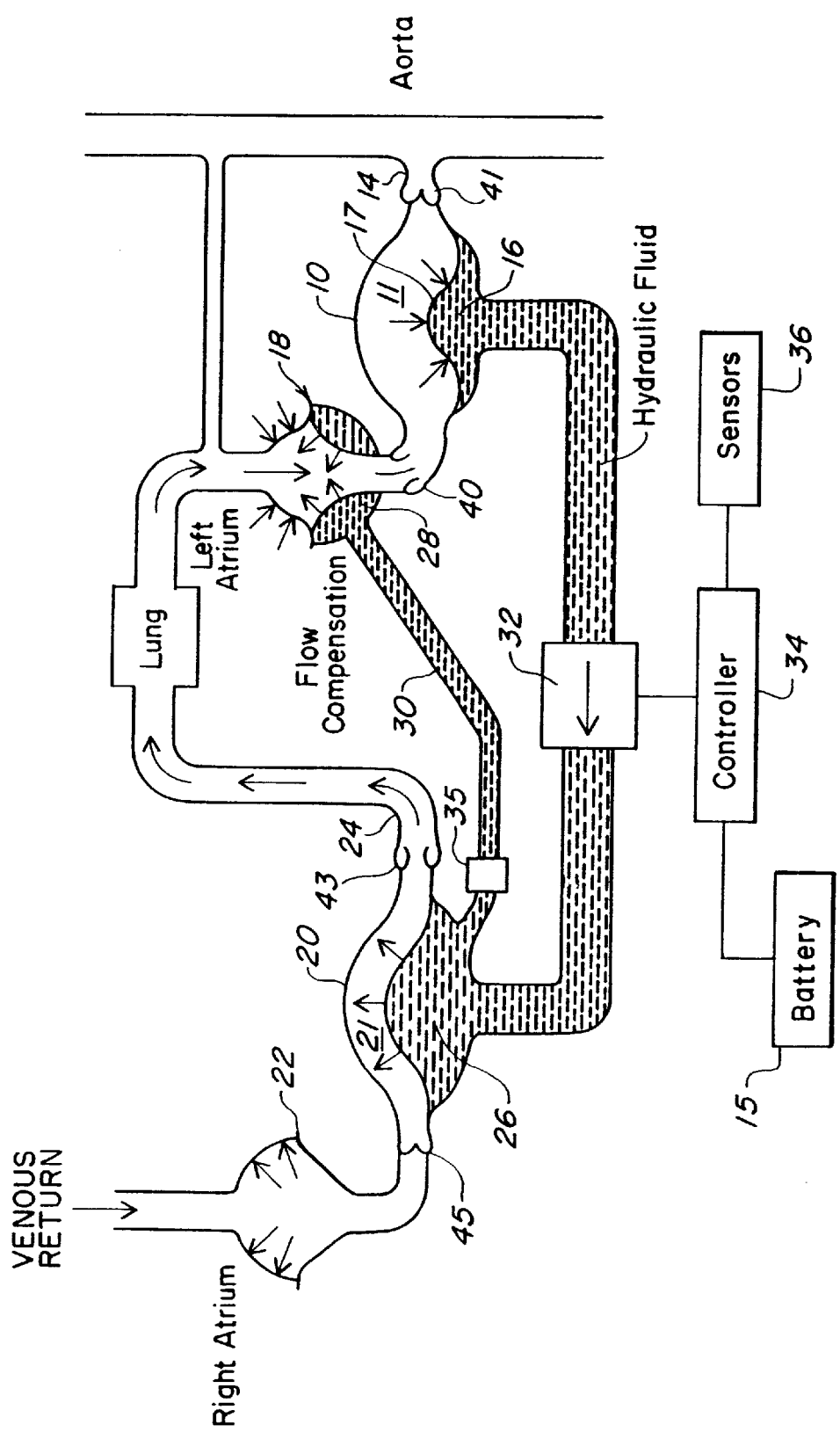
FIG. 1 illustrates diagrammatically a biventricular cardiac prosthesis of the invention during right side systole.

A block diagram of an artificial heart system in accordance with the principles of the invention implanted within a patient is illustrated in FIGS. 1 (showing the system during right side systole) and 1A (showing the system during left side systole). In this embodiment, left blood pump 10 and right blood pump 20, each with a stroke volume typically in the range of about 10 to 85 cc, are hydraulically connected to an energy converter 32 which includes both a fluid switch and a hydraulic pump as will be further described below.

The left side pump 10 includes a blood flow pumping chamber 11 having a blood input section 18 from the left atrium and a blood output port 14 to the aorta. Generally, blood input sections are constructed as atrial cuffs, which can be made, for example, from velour, and more particularly, from Dacron®, that connect the blood pumping chamber to the patient's atrium. Blood valves 40 and 41, such as trileaflet valves, have the normal valving function for the blood flow into and out of the blood pumping chamber 11. Pump 10 also includes a hydraulic pumping section 16 which is fluidically coupled to the hydraulic pump 32.

Right side pump 20 is constructed similarly to left side pump 10, having a blood pumping chamber 21 coupled between the right atrium at its blood input port 22 and the pulmonary artery at its blood output port 24 by means of blood valves 45 and 43. This pump also includes a hydraulic pumping section 26 fluidically coupled to the energy converter 32.

Figure 2:
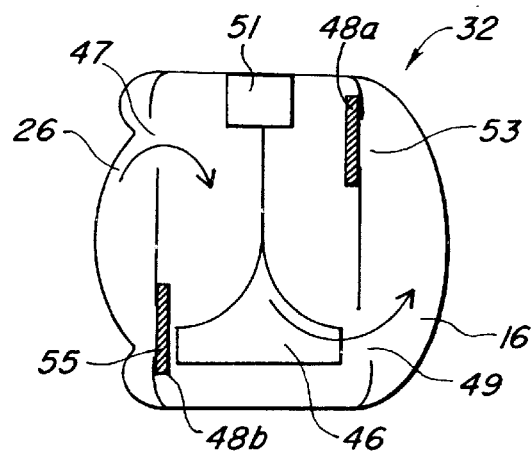
FIG. 2 illustrates an energy converter useful with the prosthesis of FIG. 1.

As illustrated diagrammatically in FIG. 2, an exemplary energy converter 32 includes a hydraulic pump 46 which is coupled through a fluid switch 48a, 48b to the hydraulic sections 16 and 26. The fluid switch and hydraulic pump in energy converter 32 are controlled by a controller 34 which receives electrical power from a battery 15 and control signals from sensors 36. In the illustrated embodiment, the hydraulic pump 46 is a centrifugal flow pump with a sleeve valve 48a, 48b which can be electrically switched. Depending upon the position of the sleeve valve, fluid is pumped either in the direction away from hydraulic section 16 and toward hydraulic section 26 or in the other position, away from hydraulic section 26 and toward hydraulic section 16.

As illustrated, the energy converter 32 is drawing hydraulic fluid from right hydraulic section 26 and directing it to left hydraulic section 16. In this embodiment, energy converter 32 includes an inlet port 47 from the right hydraulic section 26 and an outlet port 49 to the left hydraulic section 16. The hydraulic pump 46, a centrifugal pump driven by motor 51, draws hydraulic fluid into the energy converter 32 through inlet port 47 from the right hydraulic section 26, and expels the hydraulic fluid out through outlet port 49 to the left hydraulic section 16. Energy converter 32 also includes and inlet 53 from the left hydraulic section 16 and an outlet 55 to the right hydraulic section 26, but these ports are blocked by an inlet blocking portion 48a and an outlet blocking section 48b of the fluid switch. In order to reverse the direction of the fluid flow, the position of the blocking sections 48a, 48b of the fluid switch are reversed so that inlet blocking portion 48a blocks the inlet 47 from the right hydraulic section 26 and the outlet blocking portion 48b blocks the outlet 49 to the left hydraulic section 16. Where energy converter 32 is generally cylindrical, this switching may be accomplished by rotating the fluid switch 48a, 48b 180°.

Figure 1A:
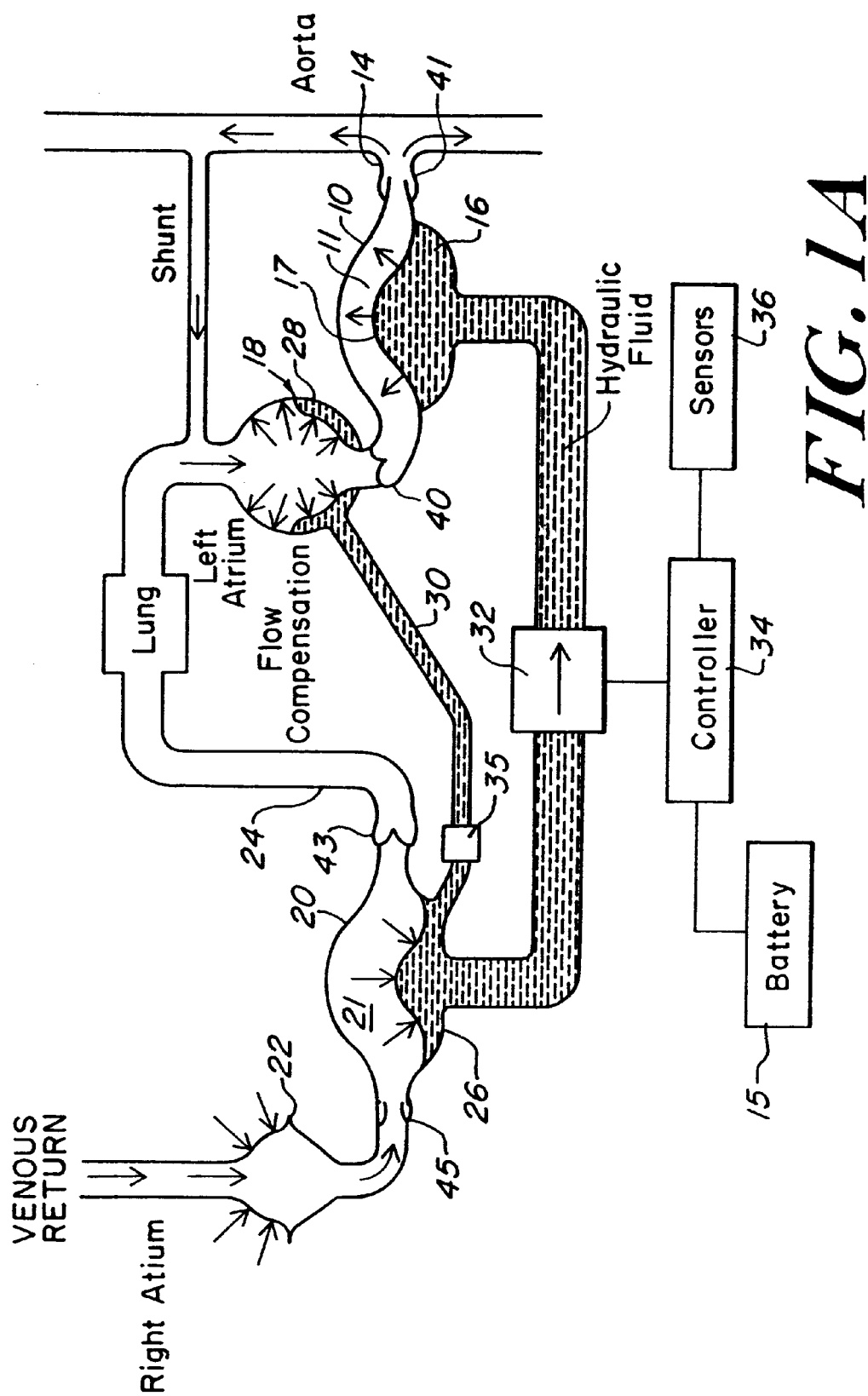
FIG. 1A illustrates diagrammatically the prosthesis of FIG. 1 during left side systole.
Figure 3:
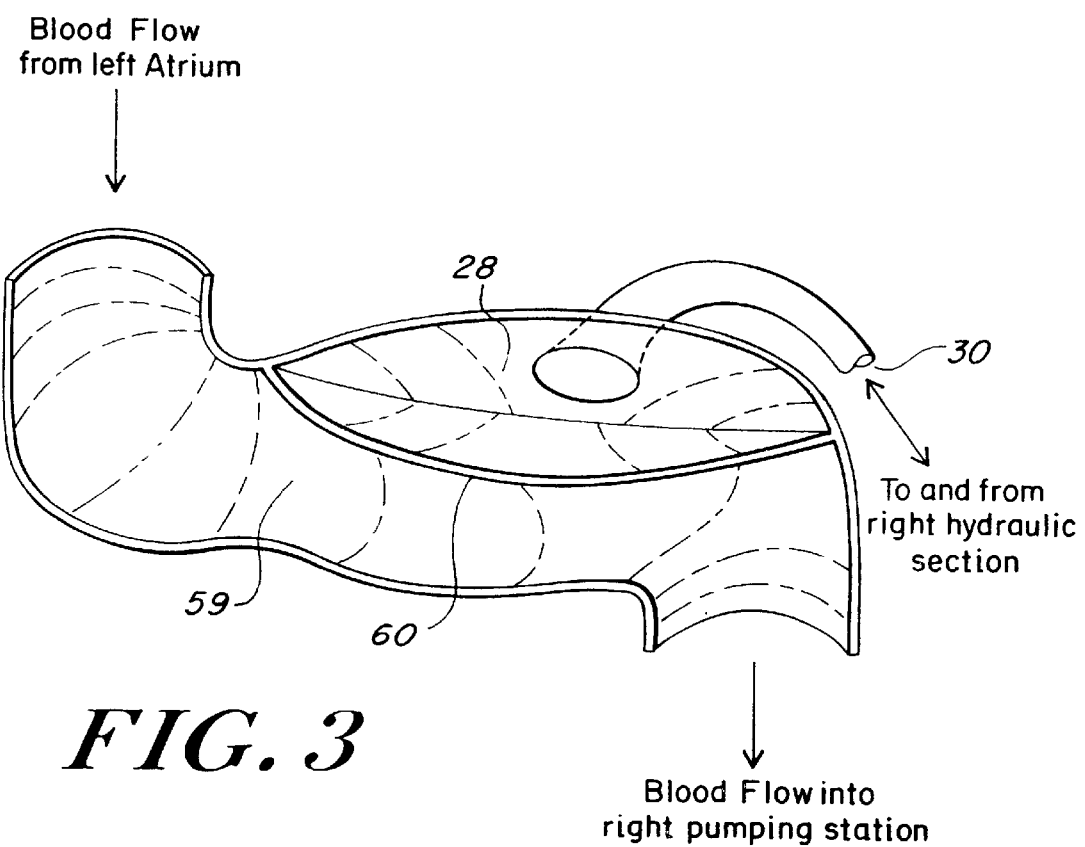
FIG. 3 illustrates an atrial blood flow conduit and hydraulic balance chamber useful with the prosthesis of FIG. 1.

The system of the invention illustrated in FIGS. 1 and 1A also includes a balance chamber 28 responsive to left atrial pressure. Hydraulic balance chamber 28 is associated with the atrial blood input 18 of the left pump 10 and is fluidically coupled through conduit 30 to the right side hydraulic section 26. The volume of hydraulic balance chamber 28 is small compared to the volume of hydraulic sections 16 and 26 (typically a 1:5 ratio). Construction of an exemplary hydraulic balance chamber 28 is illustrated in FIG. 3. In this example, a blood conducting conduit 59 connects atrial blood flow from the left atrium, via blood input 18 constructed as an atrial cuff for suturing to a patient's left atrium, and left side blood pumping section 11. In particular, it is preferable for conduit 59 to have low resistance to flow so that the blood pressure in conduit 59 is effectively equal to left atrial blood pressure. Under these conditions, diaphragm 60 is effectively responsive to blood pressure within the atrium.

Hydraulic balance chamber 28 is separated from the patient's blood flow by diaphragm 60 and is hydraulically coupled to the right side hydraulic chamber 26 through conduit 30. The position of the diaphragm 60, and thus the volume of the hydraulic balance chamber 28, varies in response to the difference between the left atrial blood pressure and the right hydraulic section 26 pressure. A person of ordinary skill in the art will recognize that construction of hydraulic chamber 28 may vary from the illustrated embodiment in keeping with the spirit of the invention. For example, hydraulic balance chamber 28 could be integral with the atrial cuff at blood input 18.

Figure 4:
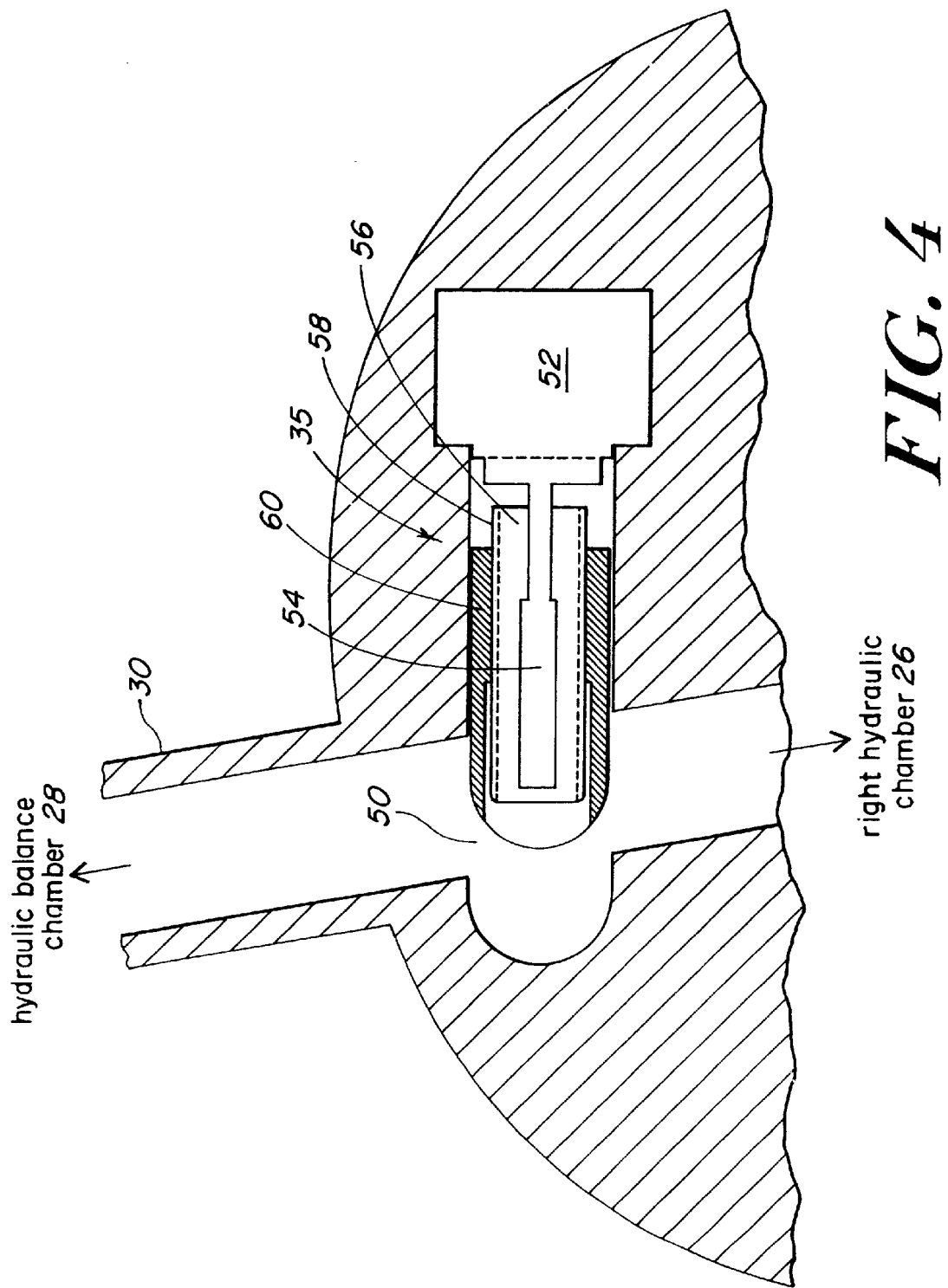
FIG. 4 illustrates an adjustable occluder useful with the prosthesis of FIG. 1.

An occluder 35 (FIGS. 1 and 1A) is coupled to conduit 30 to vary the resistance to flow (R) between the right side hydraulic chamber 26 and the hydraulic balance chamber 28. An exemplary occluder 35 is illustrated in FIG. 4. Occluder 35 is located in line with conduit 30 into the right hydraulic chamber 26 and is mounted to a translation motor 52 that moves the occluder 35 in a direction at least partially transverse to the flow path of conduit 30. The occluder 35 can be moved back and forth by translation motor 52 to vary the effective diameter of conduit 30, and thus affect hydraulic shunt flow resistance (R) through the conduit. In the illustrated embodiment, transaction motor 52 has a rotating shaft 54 connected to a drive screw component 56 having external threads 58. An occluding member 60 is threadedly engaged with the drive screw 56 so as to translate in a direction at least partially transverse to the flow path of conduit 30 upon rotation of the drive screw 56 in response to translation motor 52. A person of ordinary skill in the art will recognize that a variety of occluder devices could be used consistent with the spirit of the invention. For example, the location of the occluder along the length of the conduit could be changed, the occluder could be driven by a solenoid rather than a translation motor, the occluder could comprise an inflatable constrictor for varying the effective diameter of the conduit, or other means for varying resistance to flow could be employed.

Referring again to FIG. 1A, the pumping cycle is as follows. During left side systole, energy converter 32 is directing hydraulic fluid to left side hydraulic chamber 16, causing diaphragm 17 to move so as to expand the left hydraulic section 16. The moving of diaphragm 17 increases the pressure of the blood in the left side blood pumping chamber 11, causing valve 40 to close, valve 41 to open, and blood from the pumping chamber 11 to be expelled into the aorta.

Concurrently with left side systole, the right side blood chamber 21 is filled from the right atrium. If the blood volume filling the right pump from the right atrium is less than the volume ejected from the left side blood chamber the hydraulic balance chamber 28 adjusts its volume in response to increased left atrial pressure to accommodate this volume difference by virtue of hydraulic fluid flowing from the compensating hydraulic balance chamber 28 into the right hydraulic section 26. The shunt flow (SF) of hydraulic fluid between the hydraulic balance chamber 28 and the right side hydraulic chamber 26 thus depends on the difference between left atrial pressure and right hydraulic pressure (LAP–RHP).

During right side ejection and left pump filling (FIG. 1), the process is reversed. Energy converter 32 directs hydraulic fluid away from the left side hydraulic chamber 16 and into the right side hydraulic chamber 26 and, by virtue of conduit 30, into hydraulic balance chamber 28.

Control schemes and parameters for actively controlling occluder 35 to result in optimum resistance to flow in conduit 30 are described below. A person of ordinary skill will recognize that the control schemes can be applied to a cardiac prosthesis having the ability to vary the ratio of flow between the right and left side generally, and are not necessarily limited to the specific embodiment described above, though that embodiment will be used to illustrate the control schemes below.

Figure 5:
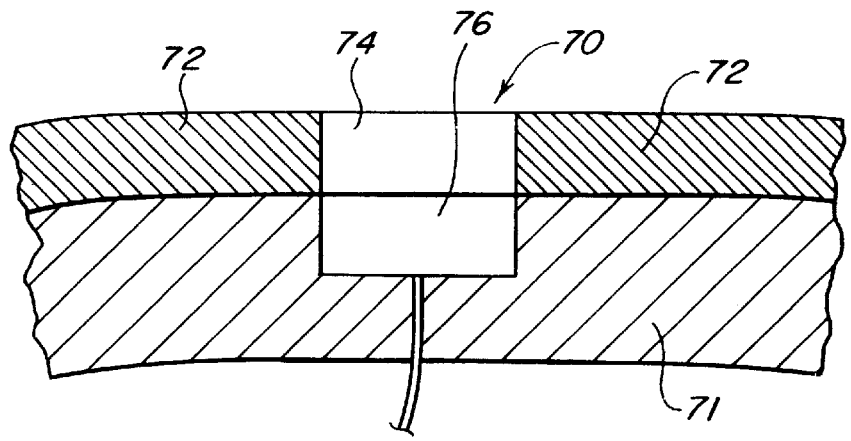
FIGS. 5 and 5A illustrate pressure sensor embodiments useful with the prosthesis of the invention.

In one control scheme embodiment, flow control is based on a control signal representing left atrial pressure (LAP) directly. In this embodiment, a pressure transducer is implanted with the prosthesis so as to be responsive to LAP. In an exemplary embodiment illustrated in FIG. 5, a pressure sensing system 70 is applied to the left atrium so that the transducer does not contact blood, or so that only a blood safe portion of the system contacts blood. To employ system 70, a housing 71 having a blood safe coating 72, such as a blood safe epoxy is implanted so as to contact blood in the left atrium. A hole in the coating is filled with a blood safe filler material 74 that allows pressure to be transmitted through to a pressure transducer 76 mounted within the housing 71. The filler material 74 must be non-toxic and non-thrombogenic, as well as supple enough to allow pressure to be transmitted to the transducer below. One such material is ANGIOFLEX™, available from ABIOMED, Inc. of Danvers, Massachusetts. Transducer 76 then provides an electronic control signal representative of LAP which can be used to control flow to maintain LAP within physiologic bounds.

Figure 5A:
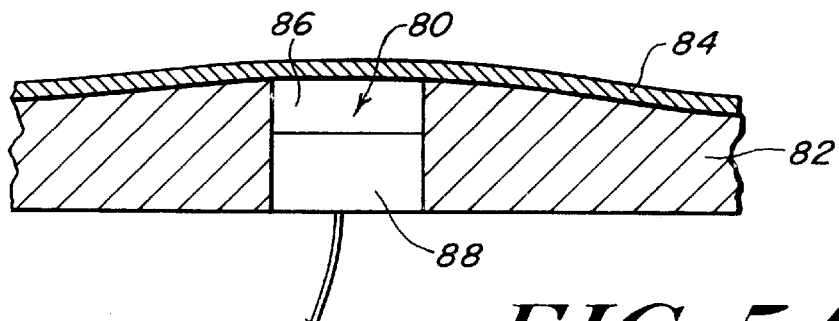

A second LAP sensor system 80 is illustrated in FIG. 5A. In this system, a housing 82 is covered by a blood contacting membrane 84. A filler material 86 is provided in a hole in the housing 82 to transmit pressure to transducer 88. A thin membrane 84 of non-toxic, non-thrombogenic material such as ANGIOFLEX™ can then be coated over the housing 82 and filler material 86. By constructing the sensor in this way, the filler material may be selected for appropriate pressure transmitting properties without concern that it will contact blood.

Having feedback on atrial pressures available, such as signals provided by sensor systems 70 or 80, a feedback control algorithm can be employed to control the system of FIG. 1 to maintain LAP within physiologic bounds. In one exemplary feedback control algorithm useful with the cardiac prosthesis illustrated in FIG. 1, the algorithm determines once in each adjustment interval period, for example every 25 beats, whether action needs to be taken to open or close the occluder 35 based on the patient's left atrial pressure. If LAP is within some tolerance around the desired LAP, no action need be taken. If LAP is out of tolerance with the desired LAP, then the occluder is adjusted until LAP is back within tolerance.

In one specific example of such an algorithm, if LAP is larger than a maximum setting, the occluder 35 is opened by a large step size, for example, by 6%. If the LAP is lower than a minimum setting, the occluder 35 is closed by a large step size. Alternatively, if LAP is larger than the desired value plus the tolerance but below the maximum, the occluder 35 is opened by a small step size, for example, by 2%. If LAP is lower than the desired value minus the tolerance, but is larger than the minimum, then the occluder 35 is closed by a small step size.

Other control algorithms could, for example, vary the step size proportionally with the distance of LAP from the desired value, or from the desired value plus or minus the tolerance. In addition, open loop gain of the feedback loop can be increased by reducing the time interval for corrections and increasing the step sizes for adjusting the occluder. In addition, the control circuitry may include a communications interface with an external control unit for the purpose of performing diagnostics, downloading historical performance data, or uploading new parameters for use in the control algorithm.

Alternatively, it may be desirable under some circumstances to implement flow control to maintain LAP within physiologic bounds without directly measuring LAP such as by using sensor systems 70 or 80. In these cases, with proper prosthesis design, it is possible to implement the flow control algorithms described above by acting on a control signal that represents the difference between LAP and RAP, without having to directly measure either. The system can then be controlled to maintain LAP with respect to RAP.

In one embodiment of such a system, a pressure sensor or sensors can be placed within the cardiac prosthesis itself to generate a signal that accurately represents the difference between LAP and RAP. This signal can then be used in a feedback control algorithm to control the left-right flow in the prosthesis to maintain LAP within physiologic bounds. In specific embodiments, sensors 66 (FIG. 6) can be placed to measure the hydraulic fluid pressure in right hydraulic section 26 and left hydraulic section 16, or a single pressure sensor 68 (FIG. 6A) may be placed in an inlet region 69 of energy converter 32 to generate a control signal that can be used to maintain LAP within physiologic bounds. Considerations for effecting this control scheme in the prosthesis of FIG. 1 are described below.

The hydraulic compliance chamber 28 illustrated in FIG. 1 has a flexible membrane coupled to the left atrial blood which partially shunts the hydraulic flow (hydraulic shunt flow=SF) of the right pump 26 to reduce the stroke volume of the right side. This hydraulic shunt flow is sensitive to the difference between LAP and the right chamber hydraulic pressure during right diastole (RHP; as used herein, RHP and LHP (left hydraulic pressure) refer to the hydraulic chamber pressures during diastole). This relationship can be represented by the following equation:

$$SF = \frac{LAP - RHP}{R} \qquad \text{Equation 1}$$

where R is the resistance to flow of the flow path connecting the compliance chamber to the right hydraulic chamber. By adding and subtracting RAP/R, equation (1) can be rewritten as:

$$SF = \frac{LAP - RAP}{R} + \frac{RAP - RHP}{R} \qquad \text{Equation 2}$$

where RAP represents the right atrial pressure. If RAP–RHP is close to zero, a properly designed low flow resistance ("R" is a low value) will result in a broad range of hydraulic shunt flow (between about 0 to 10% of the cardiac output) over a typical span of cardiac output flows (3 to 10 L/min) while maintaining LAP to within about 5 mmHg of the RAP.

However, due to pressure drops in the inflow blood conduits and through the valves, the RHP is often lower than the RAP. In some high flow conditions, RHP may be as much as 50 mmHg lower than the RAP due to these losses. Rewriting equation (2) to isolate the term (LAP–RAP) yields:

$$LAP-RAP=SF\times R-(RAP-RHP). \qquad \text{Equation 3}$$

When the quantity (RAP–RHP) is large and positive, then the term SF×R must be made large to reach the goal of keeping LAP–RAP small (≦5 mmHg). Adjustable occluder 35 is therefore used to vary the flow resistance R, and thus the value of SF×R in Equation (3).

A closed loop control system for adjusting R to maintain LAP approximately equal to RAP would involve measuring both LAP and RAP, with subsequent adjustment of R by either opening or closing the occluder to keep LAP–RAP≦5 mmHg. However, it may be desirable to implement the control scheme of the invention without directly measuring LAP and RAP on a chronic basis.

Figure 6:
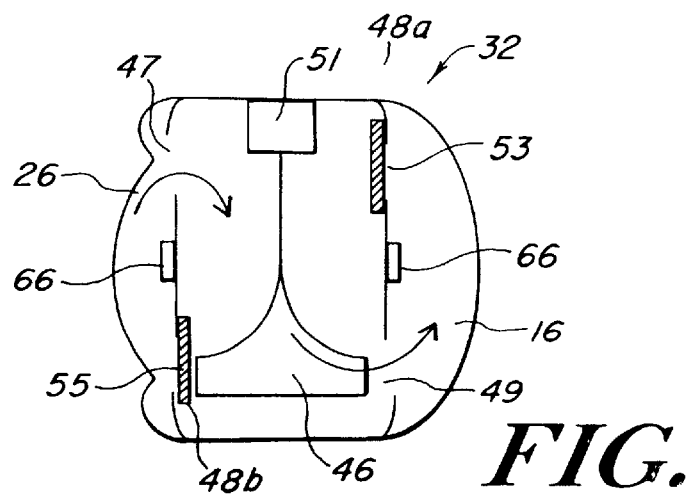
FIGS. 6 and 6A illustrate energy converters useful with the prosthesis of FIG. 1 having two and one pressure transducers, respectively.
Figure 6A:
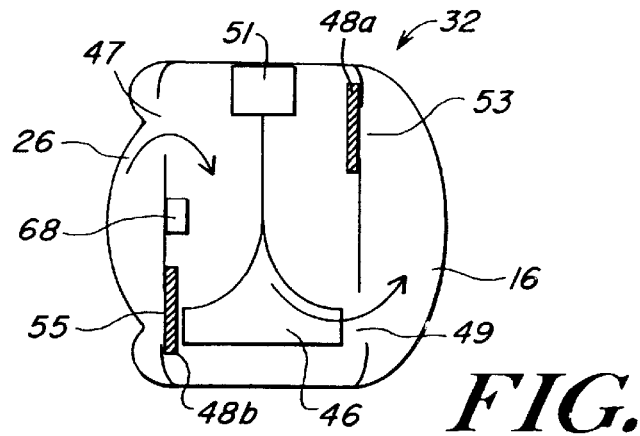

As an integral part of an exemplary cardiac prosthesis system of the invention as illustrated in the embodiment of energy converter 32 shown in FIG. 6, two hydraulic pressure sensors 66 can be provided to continuously measure the left and right hydraulic pressure in chambers 26 and 16. As noted above, a difference between atrial pressure and pump pressure on each respective side of the heart develops in high flow conditions due to pressure drops through the valves and blood flow conduits. These pressure drops can be estimated using well known "head loss" relationships for fluid flow through a system where, for a given fluid, the pressure drop is approximately proportional to the square of the fluid flow rate through the system. During the diastolic phase of each respective cycle (when the inflow valve is open and blood is flowing from the atrium into the blood pumping chamber), the relationship between the atrial pressures and the hydraulic pressures can thus be represented by:

$$LAP-LHP=a\ Q^n \qquad \text{Equation 4}$$

$$RAP-RHP=b(Q-SF)^m \qquad \text{Equation 5}$$

where Q is the total blood flow through the heart, n and m are exponents that are approximately equal to 2. The terms a and b are loss coefficients, which by component characteristics selection (flow lengths and diameters, valve characteristics, etc.) can be made nearly equal to each other. By setting the exponents equal to 2 and taking the difference of Equation 4 and 5:

$$LAP-RAP=LHP-RHP+(a-b)Q^2+2b\ SF\ Q-b\ SF^2 \qquad \text{Equation 6}$$

For a≈b by design as described above, and SF being small compared to Q (SF≈0), it is evident that by the measurement of LHP and RHP, one can derive LAP–RAP, and achieve the goal of using LAP–RAP as a control signal to guide placement of the occluder 35 to affect R so that LAP–RAP is close to zero.

Figure 7:
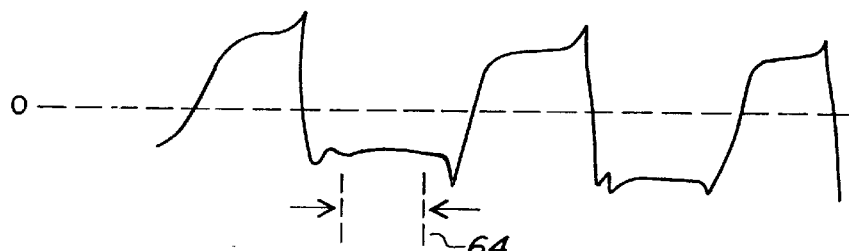
FIG. 7 is a representation of a pressure reading produced by a pressure sensor in the prosthesis of the invention.

The measurement of LHP and RHP is preferably performed during the respective diastolic phase of the left and right pumping chambers. As illustrated in FIG. 7, averaging over an appropriate time duration 64 of diastolic pressure provides a good measure of the hydraulic pressures in the right and left side hydraulic chambers during diastole for application of Equation (6). The size of averaging window 64 is selected to yield the best measurements. Noise in the pressure signal which may be present during switching from left to right pumping and vice versa can be eliminated by proper window selection. Normally, between 30% to 80% of diastole is used for averaging.

Measurements show that for total blood flows (Q) of 4 to 6.5 L/min, the correlation between LHP–RHP and LAP–RAP is quite acceptable to within 5 mmHg, indicating that the sum $(a-b)\ Q^2+2b\ SF\ Q-b\ SF^2$ is not excessive. Additionally, equation 6 can further be corrected by approximately the sum $(a-b)\ Q^2+2b\ SF\ Q-b\ SF^2$ as a piecewise linear function of Q only. This function can be determined for each cardiac prosthesis to result in a correlation between LHP–RHP and LAP–RAP that is within a few mmHg.

As total blood flow Q increases, the deviation of LHP–RHP from the true LAP–RAP is expected to increase, especially for flows greater than 9 L/min. While operating under such conditions, a momentary reduction in flow can be implemented for a short period of time for the sole purpose of measuring LHP and RHP accurately to implement balance control. To limit this time to a minimum, beat rate (BR) change (rate of switching in the fluid switch of energy converter 32) and motor speed (ω) change (speed of the hydraulic pump of energy converter 32) should be simultaneous in a proportional manner according to:

$$\frac{\Delta BR}{BR} = \frac{\Delta \omega}{\omega} \qquad \text{Equation 7}$$

to maintain smooth transitions down and up to the original flow. Testing shows that reducing flow for a 10 second duration is sufficient to perform accurate diastolic pressure measurements for the purpose of the flow control system of the invention.

For long term, chronic applications of the invention to cardiac prosthesis, it may be desirable to correct for transducer drift that may occur in the pressure transducers that measure RHP and LHP over time. One approach is to use one transducer 68 for the measurement of both sides of the diastolic pressure as illustrated in the energy converter 32 of FIG. 6A. This can be implemented by hydraulically connecting the single transducer to the inflow region 69 of the energy converter 32. Because the fluid switch of the energy converter 32 directs hydraulic fluid from whichever hydraulic pumping chamber is currently in diastole, only diastolic pressures are measured by transducer 68. Transducer 68 can then be polled during left and right diastole at separate times, and a difference between the values representing left and right hydraulic pumping chamber diastole could be taken to provide a control signal for the system. Such a one transducer system would completely bypass the sensor drift problem, since only differences in pressures are used and the sensor drift would be the same for both measurements because the same transducer is used.

In the embodiment of FIG. 6 where two transducers 66 are used, the amount of transducer drift over time may be different for each sensor. A real time calibration approach can be implemented in this situation. One real time calibration approach is to stop the hydraulic pump 46 for a short period of time (e.g., about 100 msec) at the end of right or left systole. During this period, the hydraulic pressure in the system equilibrates, that is, RHP=LHP. Measurement of the left and right hydraulic pressures at this time yields a relative transducer offset, which can be added or subtracted from the measured LHP−RHP while the system is operating.

An alternate real time calibration approach which requires no hydraulic pump 46 stoppage is to vary the motor 51 speed according to a predetermined profile, and record the pressure differences from each transducer. In one embodiment, the speed of motor 51 can stepwise slowed down at the end of systole when there is effectively no flow through the hydraulic pump 46. The motor 51 speed step down can be in steps, for example, a few hundred RPMs in time steps of few tens of milliseconds. With no flow, the pressure difference ($\Delta P$) is proportional to the square of the motor speed ($\omega$):

$$\Delta P = k\omega^2 + \text{offset} \qquad \text{Equation 8}$$

By extrapolating to $\omega=0$, the residual $\Delta P$ is the relative transducer offset.

The signals from the transducer or transducers representing left and right hydraulic pressure can be compared either digitally where the controller includes a microprocessor or other digital circuitry appropriate for this purpose, or in analog fashion, for example, using a comparator circuit to compare pressure signals from two transducers to result in a pressure difference control signal. Where a biventricular cardiac prosthesis has been constructed as described above, this control signal is representative of the difference between right and left atrial pressures. The control signal can therefore be used to adjust occluder 35 to maintain the control signal at zero, resulting in difference between right and left atrial pressures that is less than 5 mmHg, thus maintaining LAP within physiologic bounds.

A cardiac prosthesis and occluder can also be configured to keep LAP close to RAP, and thus within physiologic bounds, by using a "passive" occluder. A passive occluder, as used herein, refers to a device for changing the flow resistance of a hydraulic coupling based directly on the atrial pressures, rather than through an active controller that acts on an electronic signal representing the pressures. Such a passive occluder, which may be used in place of occluder 35 in the system of FIG. 1, is illustrated diagrammatically in FIG. 8, with a specific embodiment in an exploded view in FIG. 9 and in cross section in FIG. 10, and with a further specific embodiment illustrated in FIG. 11.

Figure 8:
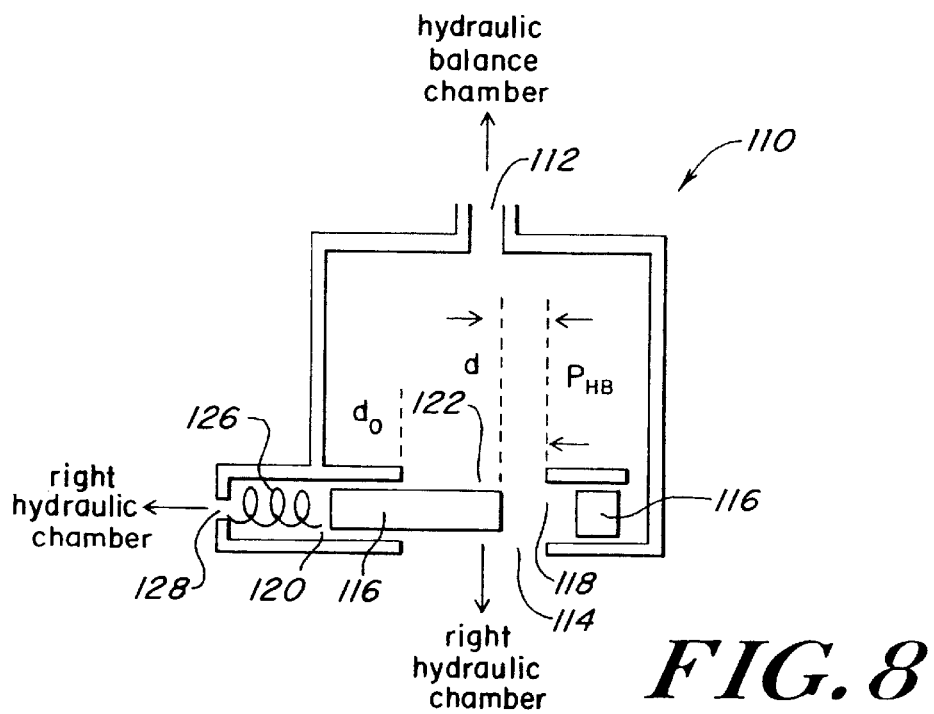
FIG. 8 is a diagrammatic view of a passively controlled occluder useful with the prosthesis of the invention.
Figure 9:
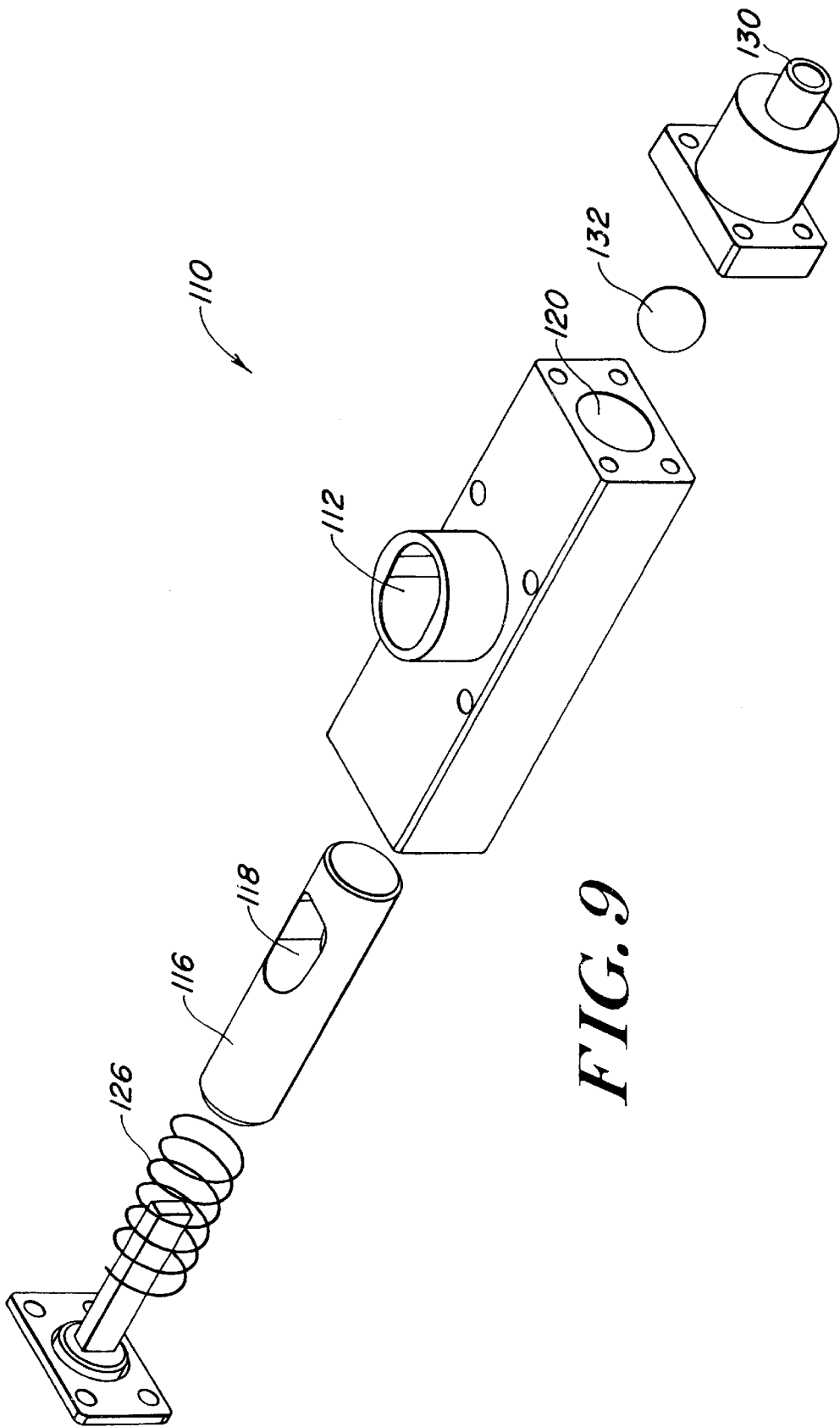
FIG. 9 is an exploded view of an embodiment of the occluder of FIG. 8.
Figure 10:
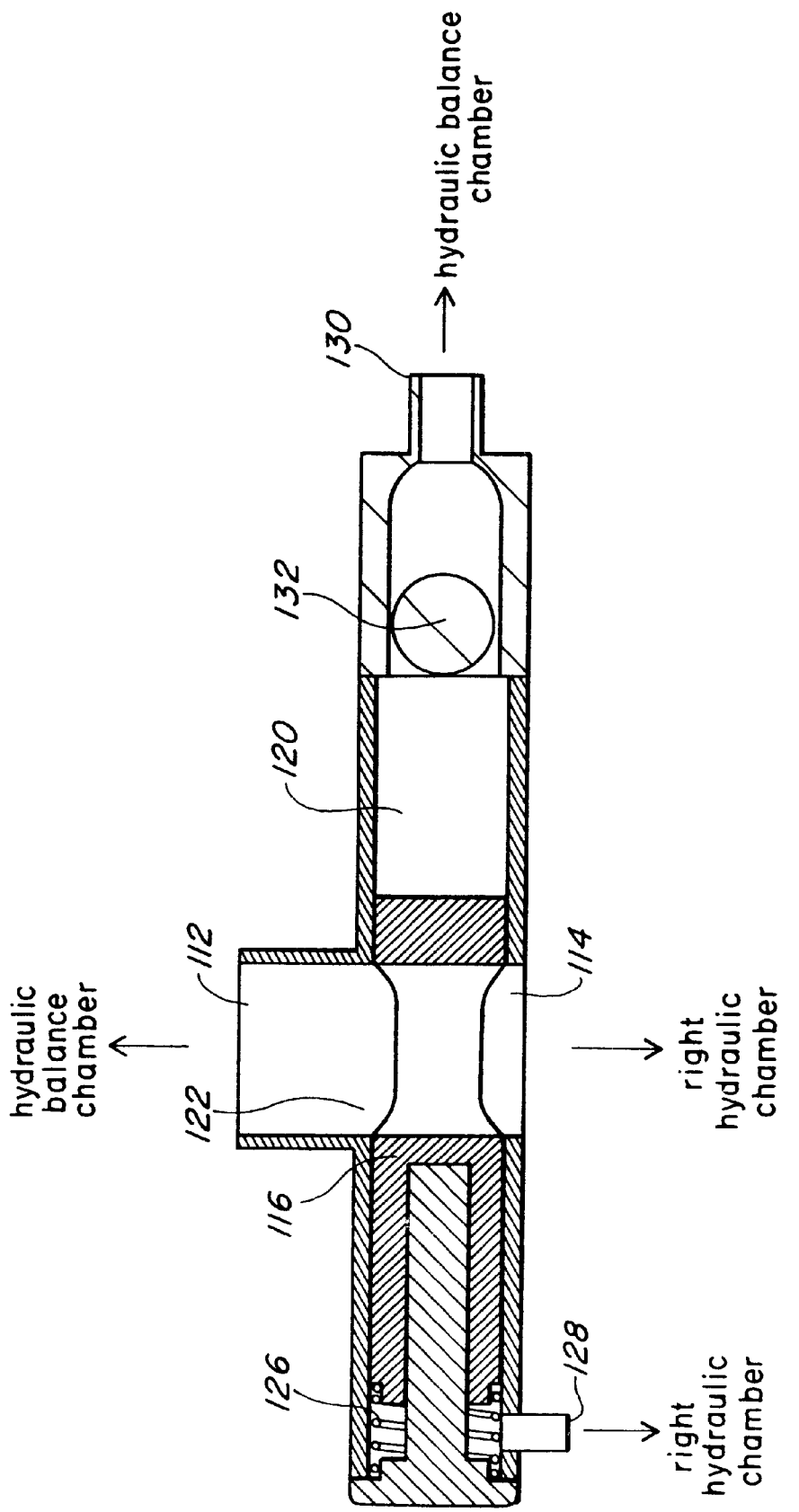
FIG. 10 is a cross sectional view of the occluder of FIG. 9.

As illustrated in FIGS. 8 to 10, a passive occluder 110 includes a port 112 to the hydraulic balance chamber 28, and a port 114 to the right hydraulic chamber 26. A piston 116 having a piston aperture 118 slides back and forth in a direction at least partially transverse to hydraulic fluid flow through the coupling 30 within a piston housing 120 that includes a piston housing aperture 122. Generally, the piston 116 is positioned within the piston housing 120 so that the overlap between the piston aperture 118 and the piston housing aperture 122 defines an occluder orifice region 124 having a length dimension "d". In order to provide the desired flow control, the orifice size is sensitive to the difference between the right and left atrial pressures. The position of the piston 116 is in part governed by a spring 126 having a spring constant $\kappa$ providing a bias on one side of the piston, and a fluidic coupling 130 providing a pressure equal to the pressure in the hydraulic balance chamber ($P_{HB}$) on the opposite side of the piston. On the spring side of the piston 116, a port 128 is also provided in fluid communication with the right hydraulic chamber, providing a pressure $P_{HR}$ on this side of the piston also.

A check valve 132 (illustrated as a ball valve in FIGS. 9 and 10) can also be provided proximate to hydraulic balance chamber port 130. Check valve 132 can mitigate the effects of right side systole on the motion of piston 132. At the onset of right systole, the pressure in the right hydraulic chamber increases rapidly as the pressure in the hydraulic balance chamber drops. Under these conditions, check ball 132 moves to block the flow of hydraulic fluid to the hydraulic balance chamber, maintaining pressure on that side of the piston throughout right systole.

In addition, a solenoid can be added to further control the motion of piston 116. For example, a solenoid coil and piston can be configured so that upon energization of the solenoid coil, piston 116 moves so as to close and stop the flow of fluid through occluder 110. The solenoid can be controlled by controller 34 (FIG. 1) so as to energize at appropriate times, such as, for example, when LAP (or LHP−RHP) is at the lower end of a target range.

Referring again to FIG. 8, occluder 110 can be designed with an equilibrium compression (a) of spring 126 that offsets the average right hydraulic pressure $P_{HR}$ when the hydraulic balance chamber pressure $P_{HB}$ is zero such that d=0. That is, when LAP approaches zero (and correspondingly, $P_{HB}$ approaches zero because of the construction of the hydraulic balance chamber 28), orifice 114 closes, hydraulic balance chamber 28 is not employed, and right side flow is not derated. This situation can be used as a boundary condition for the design of the system as illustrated in the following equation:

$$k(d+a)+A\,P_{HR}=A\,P_{HB} \qquad \text{Equation 9}$$

where A is the cross sectional area of the piston 116. The average $P_{HR}$ to which the system can be designed for d=0 and $P_{HB}=0$ is also referred to herein as $P_a$. A second boundary condition can be defined for the upper pressure limit for LAP, where the orifice should be entirely open to maximnize flow of hydraulic fluid to the hydraulic balance chamber and the derating of right side blood flow. Noting that, as described above, because of the structure of hydraulic balance chamber 28, $P_{HB}$ is a good approximation of LAP, the second boundary condition can be stated as follows:

$$kd_0=P_uA \qquad \text{Equation 10}$$

where $d_0$ is the maximum opening size of the orifice 114 and $P_u$ is the upper LAP limit, for example, 20 mmHg. These equations for the orifice size can be recast as:

$$d = d_0 + [P_{HB} - P_{HR} - (P_u - P_o)]\frac{A}{k}$$

$$d = d_0 \text{ for } P_{HB} - P_{HR} \geq P_u - P_a$$

and $$d = 0 \text{ for } P_{HB} - P_{HR} \leq -P_a$$

\hfill Equations 11

That is, the orifice will be fully open when LAP equals or exceeds RAP by a predetermined amount corresponding to the difference between the desired LAP upper limit and average RAP, and the orifice will be fully closed when LAP is less than or equal to zero.

Flow of hydraulic fluid through the orifice can be described by:

$$Q_l = \left(\frac{2\Delta P}{\rho}\right)^{1/2} wd \quad \text{Equation 12}$$

where w is the width of the orifice and wd is the area of the flow through the orifice. The discharge coefficient is assumed to be unity. The maximum orifice flow area $wd_0$ should be able to manage a flow of $Q_{l0}$ at $\Delta P_0 = P_u - P_a$ or:

$$d_0 = \frac{Q_{l0}}{w}\left(\frac{\rho}{2\Delta P_0}\right)^{1/2} \quad \text{Equation 13}$$

Substituting yields:

$$\frac{Q_l}{Q_{l0}} = \left(\frac{\Delta P}{\Delta P_0}\right)^{1/2}\left[\frac{\Delta P + P_a}{P_u}\right] \quad \text{Equation 14}$$

for $\Delta P$ between 0 and $\Delta P_0$. For $\Delta P \geq \Delta P_0$:

$$\frac{Q_l}{Q_{l0}} = \left(\frac{\Delta P}{\Delta P_0}\right)^{1/2} \quad \text{Equation 15}$$

and for d=0 or $P_{HB} - P_{HR} \leq -P_a$:

$$\frac{Q_l}{Q_{l0}} = 0 \quad \text{Equation 16}$$

The orifice size required can be calculated from Equation (13) for a rectangular shape. With w=0.2 cm, $d_0$=0.6 cm for a peak balance flow of 2 L/min or a mean flow of 0.8 L/min. The spring constant for the spring can be calculated from Equation (10). For A, the piston area of about $4 \times 10^{-2}$ cm$^2$, and $P_u$=20 mmHg, $\kappa$ is $\approx 1.8 \times 10^3$ dynes/cm or 0.01 lb/in.

Preferably, the piston should not pulse significantly during a beat. Pulsing can be avoided if the movement of the piston is limited to less than 1% of $d_0$ during half a beat. At 120 BPM, this time interval $\Delta t \sim 0.25$ sec. To achieve this, the gap ($\delta$) between the variable orifice piston and its housing should be governed by:

$$\pi r^2 \frac{\Delta d}{\Delta t} = \Delta P \frac{2\pi r \delta^3}{12\,\mu l} \quad \text{Equation 17}$$

In this equation, r, the radius of the piston, is $\approx 0.1$ cm, l, the length of the piston, is ~0.5 cm, and $\mu$, the viscosity of the hydraulic fluid, is ~0.0 poise. For $\Delta d \approx 0.1\, d_0$, and $\Delta P \sim 30$ mmHg, $\delta$ is $1.2 \times 10^{-3}$ cm or 0.5/1000 inches. A tight gap is thus not required to eliminate orifice oscillation.

Figure 11:
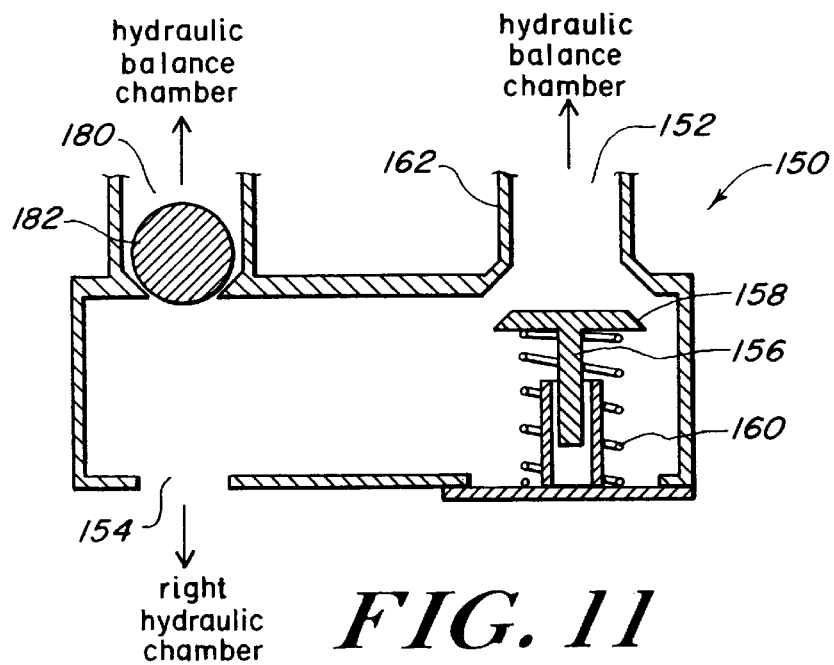
FIG. 11 is a cross sectional view of an additional passively controlled occluder embodiment useful with the invention.

An alternative passive occluder 150 is illustrated in FIG. 11. Occluder 150 includes a port 152 to the hydraulic balance chamber 28, and a port 154 to the right hydraulic chamber 26. Rather than carrying an orifice that is in-line with the flow of hydraulic fluid through the occluder, piston 156 carries a check valve member 158 that is generally transverse to the flow of hydraulic fluid in the coupling 162. The location of piston 156 depends on the constant of spring 160 and the right hydraulic pressure on one side of the check valve member 158, and the hydraulic balance chamber pressure on the opposite side of the check valve member to set flow resistance through the device.

It may also be desirable, for any of the control systems described above having a hydraulic balance chamber, to ensure that the hydraulic balance chamber is filled at the start of every beat, and drained during each beat based on the difference between LAP and RAP as measured by the system. In order to insure that the balance chamber is in the fully filled position at the start of every beat, a one way check valve can be incorporated so that during right side systole no restriction is encountered in filling the balance chamber. Referring again to FIG. 11, an occluder system 150 may include a parallel path for filling the hydraulic balance chamber without resistance during right systole by providing a balance chamber filling port 180 having a check valve 182. Check valve 182 allows resistance free filling of the hydraulic balance chamber, but forces the balance chamber to be emptied through the variable orifice through a resistance that is responsive to LAP–RAP. This parallel path can be provided as part of the occluder system as illustrated in FIG. 11, or it can be a separate, parallel fluid coupling.

One advantage of this embodiment is that the effects of right systole on piston 156 and check valve member 158 need not be compensated for. That is, during right systole, right hydraulic chamber pressure will cause check valve member 158 to close fluid coupling 162 to the hydraulic balance chamber. In the embodiment of FIG. 9, this reaction to right side systole is checked by ball valve 132 and by the piston damping characteristics. In the embodiment of FIG. 11, however, because filling check valve 182 permits filling of the hydraulic balance chamber during right side systole even when check valve member 158 is closed, check valve member 158 can be allowed to open and close freely during the beating of the cardiac prosthesis.

A fail safe mechanism can also be incorporated into an occluder system of the invention by adding a small fixed orifice between the hydraulic balance chamber and the right hydraulic chamber with a fixed resistance of 40 mmHg/L/min so that if the movable piston jams, a mean flow of up to 0.2 to 0.3 L/min could be provided within physiologic pressures.

Figure 12:
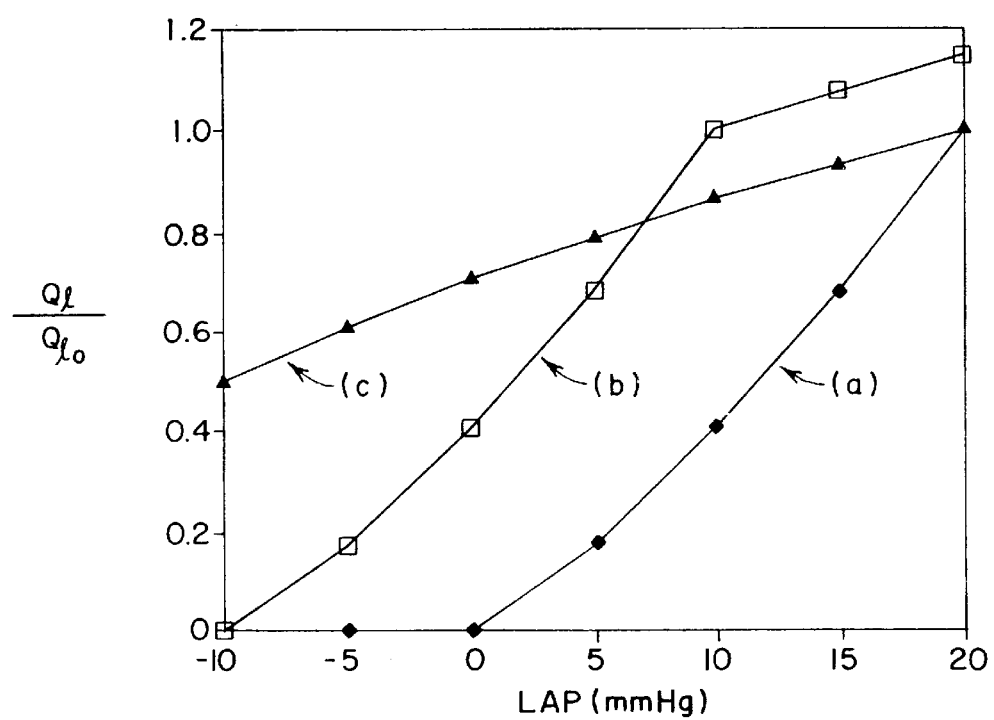
FIG. 12 is a chart showing improved flow in a prosthesis of the invention.

FIG. 12 illustrates the flow equations above for a passive occluder for three different scenarios. In scenario (a), $P_a$=−10 mmHg (setting for spring constant), $P_u$20 mmHg (upper limit for LAP), and an actual offset pressure of $P_{HR}$=−10 mmHg, resulting in $\Delta P_0$=−30 mmHg. Scenario (b) is the same as scenario (a), but with actual $P_{HR}$=−20 mmHg. Scenario (c) is a case without variable orifice control. The figure shows a much broader range of flows through the orifice in response to changing LAP in the variable orifice scenarios (a) and (b), as compared to scenario (c) which does not employ variable orifice control.

Figure 13:
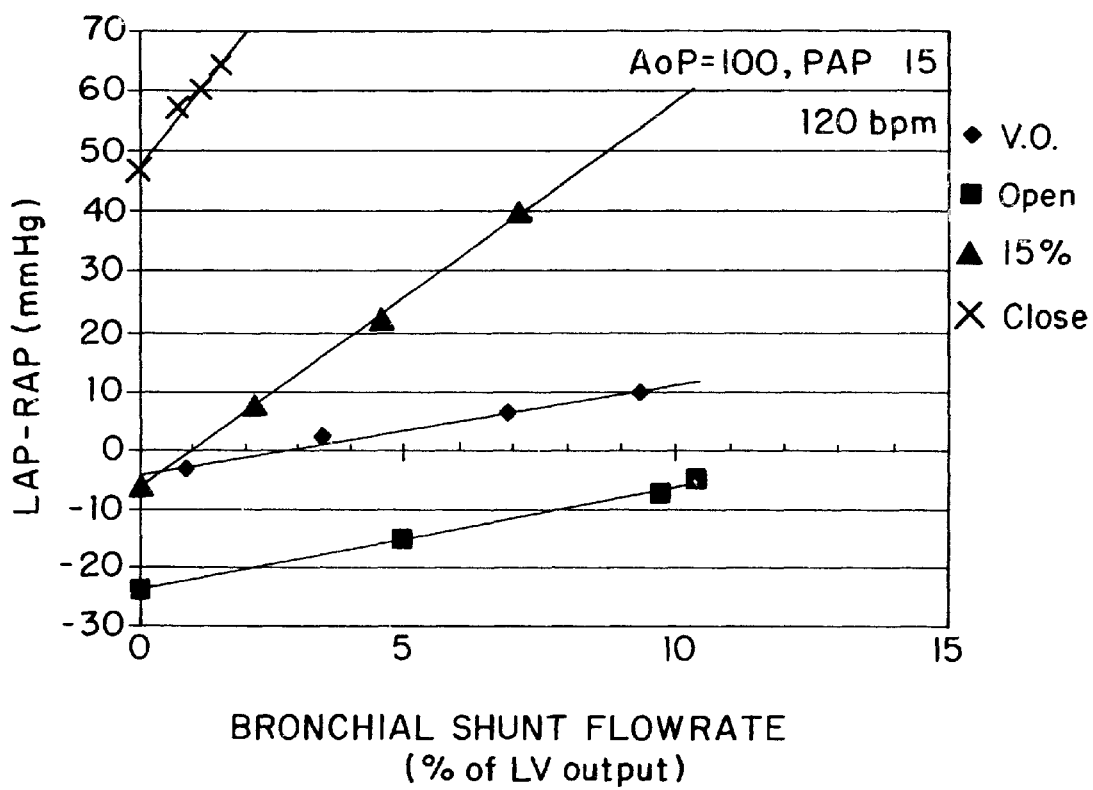
FIG. 13 is a chart showing improved pressure characteristics in a prosthesis of the invention.

Further evidence of the improvements provided by the invention is illustrated in FIG. 13. FIG. 13 shows the variation of LAP-RAP for varying bronchial shunt flow rates with the variable orifice occluder (V.O.) compared to an adjustable occluder set to three different fixed openings, namely, full open, 15% open, and fully closed. FIG. 13 shows that the variable orifice occluder keeps LAP–RAP much closer to zero than the compared situations.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. In a biventricular cardiac prosthesis having left and right pumping sections that produce left and right side blood flow, a method for maintaining a patient's left atrial pressure within physiologic bounds, comprising the steps of:

measuring the patient's left atrial pressure;

determining whether the patient's left atrial pressure is outside of a tolerance around a desired left atrial pressure;

adjusting the flow of the right pumping section to bring the patient's left atrial pressure within the tolerance wherein when the left atrial pressure is higher than the tolerance, right side flow is decreased, and when the left atrial pressure is lower than the tolerance, right side flow is increased.

2. The method of claim 1, wherein measuring the patient's left atrial pressure produces an electric signal representative of the pressure for determining whether the left atrial pressure is within tolerance.

3. The method of claim 2, further comprising the step of calculating a control signal based on the determination of whether the patient's left atrial pressure is within tolerance.

4. The method of claim 3, wherein the flow of the right pumping section is adjusted by shunting a hydraulic fluid from the right pumping section to a hydraulic balance chamber.

5. The method of claim 4, wherein the shunting is controlled by applying the control signal to adjust the flow resistance of a hydraulic coupling between the right pumping section and the hydraulic balance chamber to thereby effect the amount of shunting.

6. The method of claim 5, wherein the flow resistance of the coupling is adjusted by applying the control signal to vary the effective size of an adjustable orifice positioned in line with the coupling.

7. The method of claim 3, wherein left atrial pressure is measured by placing a pressure sensor in contact with the patient's left atrial blood flow to determine the pressure thereof.

8. The method of claim 7, wherein the flow of the right pumping section is adjusted by shunting a hydraulic fluid from the right pumping section to a hydraulic balance chamber, the shunting being controlled by applying the control signal to adjust the flow resistance of a hydraulic coupling between the right pumping section and the hydraulic balance chamber to thereby effect the amount of shunting.

9. The method of claim 8, wherein the flow resistance of the coupling is adjusted by applying the control signal to vary the effective size of an adjustable orifice positioned in line with the coupling.

10. The method of claim 3, wherein left atrial pressure is measured as a difference from a patient's right atrial pressure.

11. The method of claim 10, wherein each of the left and right pumping sections includes a hydraulic pumping section and a blood pumping section, the left atrial pressure being measured with respect to the right atrial pressure by measuring a diastolic pressure in the left and right hydraulic pumping sections and taking a difference therebetween.

12. The method of claim 11, wherein the left and right blood pumping sections are configured to provide substantially equal pressure drops for blood flowing through the pumps during pumping.

13. The method of claim 12, wherein the hydraulic pumping sections are driven by a fluid pump and a fluid switch, the left and right diastolic pressure readings being taken by a single pressure transducer coupled to an inlet of the fluid switch.

14. The method of claim 11, wherein the left and right blood pumping sections are configured to provide different pressure drops for blood flowing through the respective pumps during pumping and the left atrial pressure measurement signal comprises a component representing a difference between left and right atrial pressures and an offset component representing the difference in pressure drops.

15. A total artificial heart with balanced flow for comprising:

a right pumping section having a blood pumping chamber connectable to a patient's right atrium for blood inflow and connectable to a patient's pulmonary artery for blood outflow, and a hydraulic pumping section;

a left pumping section having a blood pumping chamber connectable to a patient's left atrium for blood inflow and connectable to a patient's aorta for blood outflow, and a hydraulic pumping section;

a reciprocating pump causing hydraulic fluid to flow between the right and left hydraulic pumping sections;

a sensor connectable to a patient's left atrium for measuring left atrial pressure;

a derating element coupled to the right hydraulic pumping section for derating right side pumping volume; and a controller responsive to the measured left atrial pressure and selectively derating right side pumping volume to maintain a patient's left atrial pressure within physiologic bounds.

16. The total artificial heart of claim 15, wherein the derating element coupled to the right hydraulic pumping section is a hydraulic balance chamber.

17. The total artificial heart of claim 16, wherein the hydraulic coupling between the right hydraulic pumping chamber and the hydraulic balance chamber includes a variable orifice for adjusting fluid resistance for hydraulic fluid flow through the coupling in response to the controller.

18. The total artificial heart of claim 17, wherein the controller includes control logic to determine whether a patient's left atrial pressure is outside of a tolerance around a desired left atrial pressure, and adjust the variable orifice to increase fluid resistance in the coupling and thereby reduce the derating of right side pumping volume when the measured left atrial pressure is below the tolerance, and adjust the variable orifice to decrease fluid resistance in the coupling to thereby increase the derating of right side pumping volume when the measured left atrial pressure is above the tolerance.

19. The total artificial heart of claim 18, wherein the variable orifice comprises an occluder movable in a direction transverse to fluid flow through the balance chamber coupling and mounted to a translation motor, the controller controlling motion of the translation motor to selectively vary an effective diameter of the balance chamber coupling whereby resistance to flow is varied.

20. The total artificial heart of claim 16, wherein the hydraulic balance chamber includes a membrane connectable to a patient's left atrium whereby the hydraulic balance chamber pressure is an analogue of left atrial pressure.

* * * * *